(12) United States Patent
Loch et al.

(10) Patent No.: US 6,174,332 B1
(45) Date of Patent: *Jan. 16, 2001

(54) ANNULOPLASTY RING WITH CUT ZONE

(75) Inventors: Deborah A. Loch, St. Paul; Kimberly A. Anderson, Eagan; Darrin J. Bergman, Shoreview; Mary G. Melcoch, Oakdale, all of MN (US)

(73) Assignee: St. Jude Medical, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/986,046

(22) Filed: Dec. 5, 1997

(51) Int. Cl.$^7$ ....................................... A61F 2/24
(52) U.S. Cl. ............................................. 623/2.37
(58) Field of Search ............................ 623/2, 2.36, 2.37

(56) References Cited

U.S. PATENT DOCUMENTS

| | | | |
|---|---|---|---|
| 3,656,185 | 4/1972 | Carpentier . | |
| 3,839,741 | 10/1974 | Haller | 3/1 |
| 4,042,979 | 8/1977 | Angell | 3/1.5 |
| 4,055,861 | 11/1977 | Carpentier et al. | 3/1.5 |
| 4,106,129 | 8/1978 | Carpentier et al. | 3/1.5 |
| 4,204,283 | 5/1980 | Bellhouse et al. | 3/1.5 |
| 4,489,446 | 12/1984 | Reed | 3/1.5 |
| 4,917,698 | 4/1990 | Carpentier et al. | 623/2 |
| 5,011,481 | 4/1991 | Myers et al. | 606/1 |
| 5,041,130 | 8/1991 | Cosgrove et al. | 623/2 |
| 5,061,277 | 10/1991 | Carpentier et al. | 623/2 |
| 5,064,431 | 11/1991 | Gilbertson et al. | 623/2 |
| 5,104,407 | 4/1992 | Lam et al. | 623/2 |
| 5,123,918 | 6/1992 | Perrier et al. | 623/2 |
| 5,171,263 | 12/1992 | Boyer et al. | 623/2 |
| 5,201,880 | 4/1993 | Wright et al. | 623/2 |
| 5,236,448 | 8/1993 | Angelini et al. | 623/2 |
| 5,258,021 | 11/1993 | Duran | 623/2 |
| 5,306,296 | 4/1994 | Wright et al. | 623/2 |
| 5,350,420 | 9/1994 | Cosgrove et al. | 623/2 |
| 5,376,112 | 12/1994 | Duran | 623/2 |
| 5,443,501 | 8/1995 | Barmada | 623/2 |
| 5,549,665 | 8/1996 | Vesely et al. | 623/2 |
| 5,593,424 | * 1/1997 | Northrup | 623/2 |
| 5,593,435 | * 1/1997 | Carpentier | 623/2 |
| 5,674,279 | * 10/1997 | Wright | 623/2 |
| 5,674,280 | * 10/1997 | Davidson | 623/2 |
| 5,776,189 | * 7/1998 | Khalid | 623/2 |

* cited by examiner

*Primary Examiner*—Michael J. Milano
(74) *Attorney, Agent, or Firm*—Hallie A. Finucane, Esq.; Westman, Champlin & Kelly, P.A.

(57) ABSTRACT

An annuloplasty ring includes an elongated main body having a generally partial shape extending between first and second ends. An elongated secondary body also includes first and second ends which couple to, respectively, the first and second ends of the main body. A first cut zone couples the first end of the main body to the first end of the secondary body. A second cut zone couples the second end of the main body to the second end of the secondary body. The annuloplasty ring may be selectively formed generally into a partial annuloplasty ring shape by severing the first and second cut zones and removing the secondary body.

14 Claims, 5 Drawing Sheets

ANNULOPLASTY RING WITH CUT ZONE

FIELD OF THE INVENTION

The present invention relates to a prosthetic support used to correct defects in a heart valve of a heart. More specifically, the present invention relates to an annuloplasty ring prosthesis for implantation around a heart valve.

BACKGROUND OF THE INVENTION

Annuloplasty rings are used to provide support to surgically corrected defects in natural valves of a patient's heart. The valves in the human heart, and in particular the mitral and tricuspid valves, include valve cusps or leaflets which are attached to the wall of the heart by fibrous chords. However, defects in the heart valve and surrounding tissue can reduce the efficiency of the heart in pumping blood. For example, if the annulus of a heart valve dilates due to disease, the valve cusps cannot completely close. This allows blood to regurgitate through the valve and greatly reduces the efficiency of the heart.

One technique of repairing a defective natural heart valve is to completely replace the valve. Valve replacements include both mechanical heart valves and bioprosthetic heart valves. However, such surgery requires the natural valve to be excised. In many instances it would be preferable to retain the natural valve by repairing the valve. For a number of reasons, it is desirable to retain the natural heart valve if possible.

A native valve repair procedure utilizing an annuloplasty ring is a desirable alternative to replacement valves in that the repair procedure does not require excision of the natural valve. Various types of annuloplasty rings are described in the prior art including rigid rings and flexible rings. For example, U.S. Pat. No. 5,061,277, issued Oct. 29, 1991 to Carpentier et al., entitled "FLEXIBLE CARDIAC VALVULAR SUPPORT PROSTHESIS" is an example of one such annuloplasty ring. Flexible annuloplasty rings allow the heart to follow a more physiological movement during systole and diastole. Additionally, the native mitral annulus is not a flat plane, and the anterior portion of the mitral annulus is curved. Such flexibility is particularly beneficial when the heart is operating at higher capacities. Traditionally, annuloplasty rings have a generally full annular configuration. The full annuloplasty ring is sutured to the tissue annulus of the natural heart valve. The ring provides support to the valve annulus or repaired valve to thereby maintain the shape of the repaired heart valve by preventing dilation of the annulus.

Recently, annuloplasty rings have been designed with a partial annular configuration. One such design is described in U.S. Pat. No. 5,041,130. Such a partial annular configuration may allow limited expansion of the natural annulus during diastole. The partial annular configuration has no anterior portion which allows the natural mitral annulus shape to be preserved in this area and to function naturally.

The anterior portion of the mitral annulus does not dilate with disease processes. Therefore, there is no need for the annuloplasty device to address this area. Not placing sutures in the anterior portion of the annulus eliminates the possibility of deforming or injuring, with sutures, the aortic valve leaflets which are in fibrous continuity with the anterior portion of the mitral valve. The decision to support the anterior portion of the annulus must be made by the surgeon on a case by case basis, and is frequently not apparent until the natural valve and surrounding cardiac anatomy is visibly inspected during surgery. Likewise, a partial ring can be used to repair the tricuspid valve to eliminate any negative effects of placing the suture in or near the AV-node.

SUMMARY OF THE INVENTION

The present invention provides an annuloplasty ring which may be implanted either as a full annular ring or as a partial ring. The annuloplasty ring includes an elongated main body having a generally partial annular configuration which extends between a first end and a second end. An elongated secondary body includes a first end and a second end extending between respective first and second ends of the elongated main body. In one embodiment of the invention, the elongated main body and the elongated secondary body are formed of flexible materials. A cut zone couples the first end of the main body to the first end of the secondary body. The cut zone may be severed, thereby forming an annuloplasty ring having a generally partial annular configuration. However, if the zone is not severed, the annuloplasty ring may be employed with a generally full annular configuration. The cut zone may extend through the entire length of the secondary body thereby forming a single elongated cut zone. Further, the cut zone may extend into the elongated main body.

DETAILED DESCRIPTION OF THE PREFERRED EMBODIMENTS

The present invention includes an annuloplasty ring which selectively provides either a full annular or 'D' shape geometry or a partial annular or 'C' shape geometry ring. Annuloplasty rings in accordance with the present invention may be modified by a surgeon after the surgeon performs a visual inspection of the native heart valve. Further, the surgeon may select the circumference of the partial annular configuration to thereby optimize the circumference of the annuloplasty ring for a particular patient's valve annulus.

Figure 1:
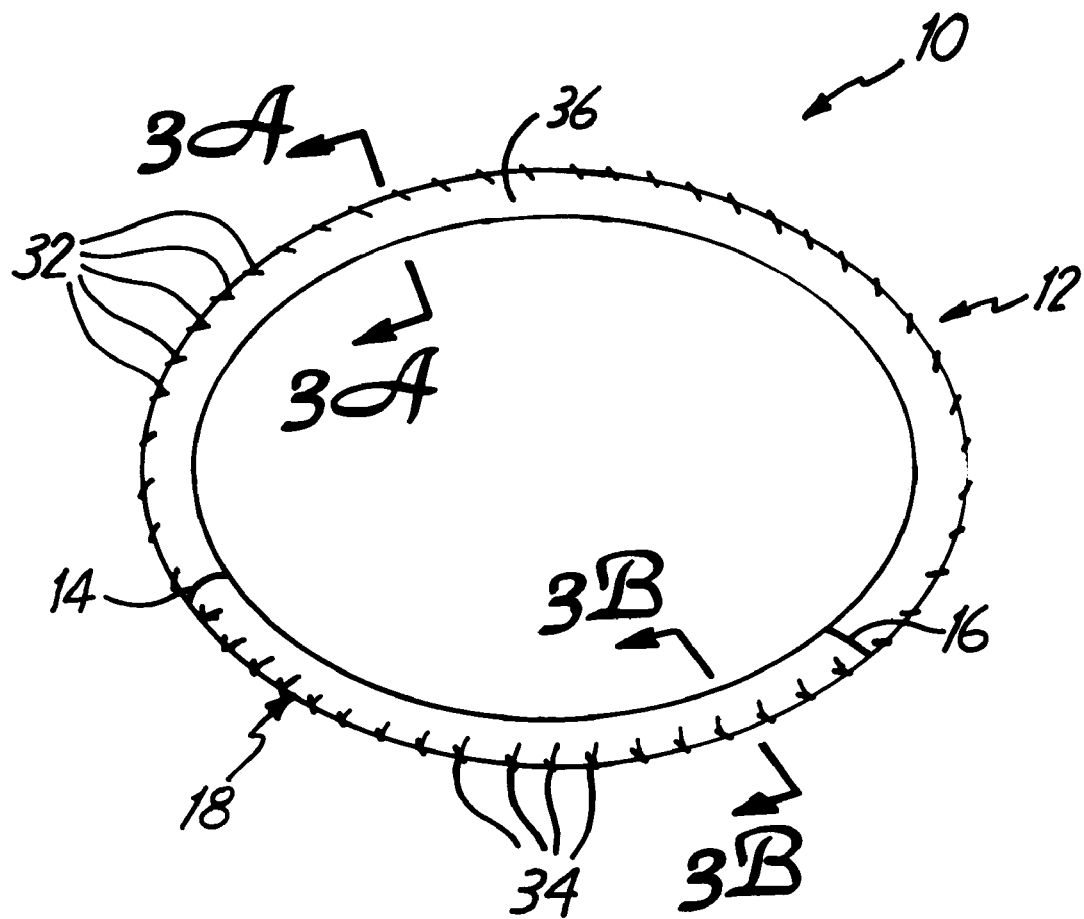
FIG. 1 is a top plan view of an annuloplasty ring in accordance with the present invention having a full annular configuration.

FIG. 1 is a top plan view of an annuloplasty ring 10 in accordance with one embodiment of the present invention. Annuloplasty ring 10 has a full annular configuration. Note that as used herein, a full or 'D' shaped configuration is intended to refer to any shape annuloplasty ring which provides a complete annulus. Further, as used herein a partial or 'C' shape annuloplasty ring refers to any annuloplasty ring which provides only a partially complete annulus.

Annuloplasty ring 10 includes an elongated main body 12 having a generally partial annular configuration which extends between a first cut zone or cut zone marker 14 and a second cut zone or cut zone marker 16. An elongated secondary body 18 extends between a first marker 14 and a second marker 16. The elongated secondary body 18 completes the annulus of annuloplasty ring 10 to thereby form a full ring. Cut zone markers 14 and 16 identify the ends of the elongated main body 12.

Annuloplasty ring 10 is formed from an outer layer 36 which is typically a fabric, such as polyester, shaped into tubular form creating an inner layer 60 (FIG. 3). Both layers are stitched together using a suture, which is indicated generally at stitching 32 and 34. Stitching 34 and internal stitching 53 are formed in a series of individual knots in secondary body 18. In some embodiments, the knots may extend through the secondary body 18 and partially into main body 12. Stitches 32 and 52 are positioned to maintain the inner layer 60 and outer layer 36 around a core (not shown in FIG. 1) of ring 10. However, in accordance with one aspect of the present invention, if secondary body 18 is severed within the defined markers 14 and 16, the knotting of stitches 34 and 53 prevents the suture and the outer layer 36 and inner layer 60 from fraying. Thus, the knots of stitches 34 and 53 act as a body retaining member to maintain the integrity of the outer layer 36 and inner layer 60.

Figure 2:
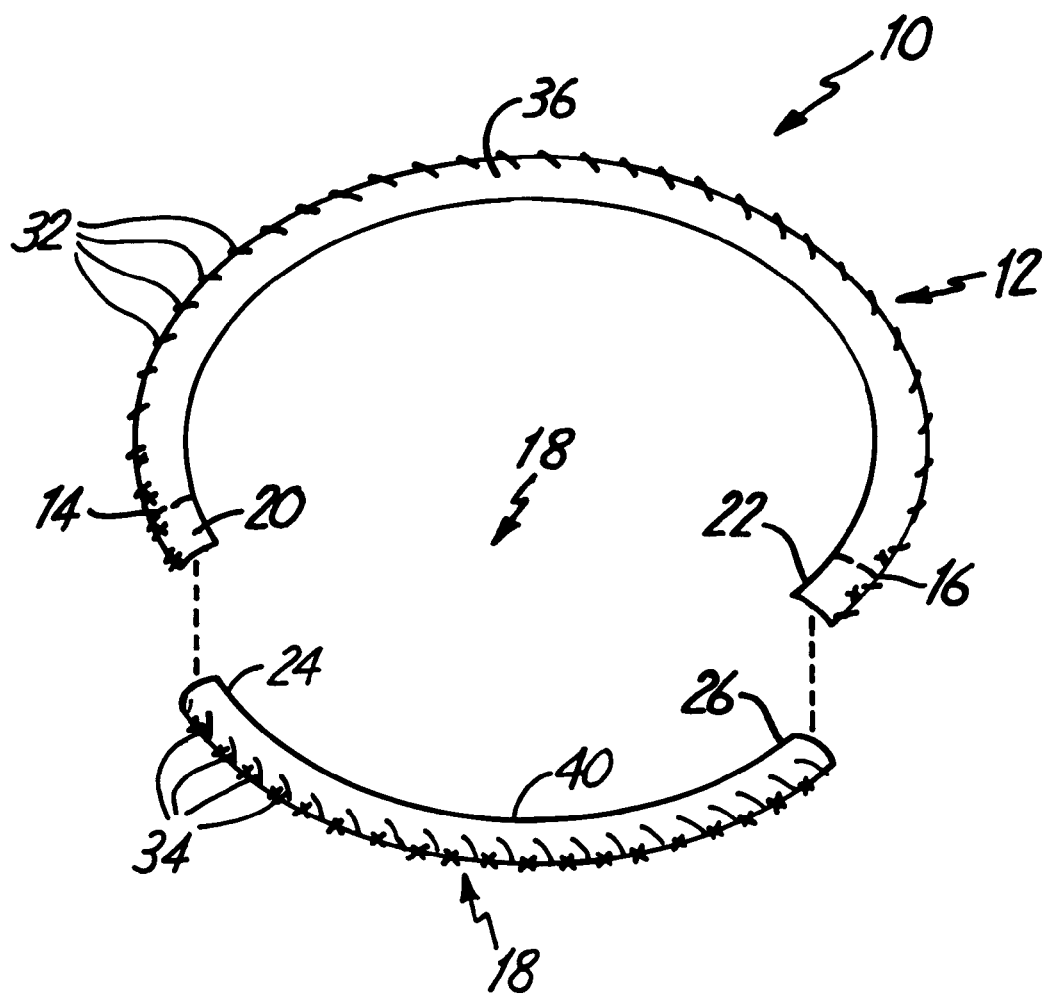
FIG. 2 is a top plan view of the annuloplasty ring of FIG. 1 having a portion removed thereby forming a partial annular configuration.

FIG. 2 is a top plan view of annuloplasty ring 10 after the cuts have been made between or at first marker 14 and second marker 16 thereby removing a portion 40 of the elongated secondary body 18. The cuts form ends 20, 22, 24, and 26. Further, stitching 34 includes relatively long stitches which are clearly visible and provide an additional cut zone markings.

In accordance with the present invention, upon removal of portion 40 ends 20, 22, 24 and 26 are prevented from unraveling or fraying by knotted stitches 34 and 53. Any appropriate knotting technique may be used, for example, knots which are typically used by surgeons to secure sutures, or a simple cinch knot. Further, any type of body retaining member may be employed to maintain the integrity of the body of annuloplasty ring 10 and prevent fraying of the body or fraying of the suture, such as staples, adhesives, ultrasonics welding, etc.

Figure 3A:
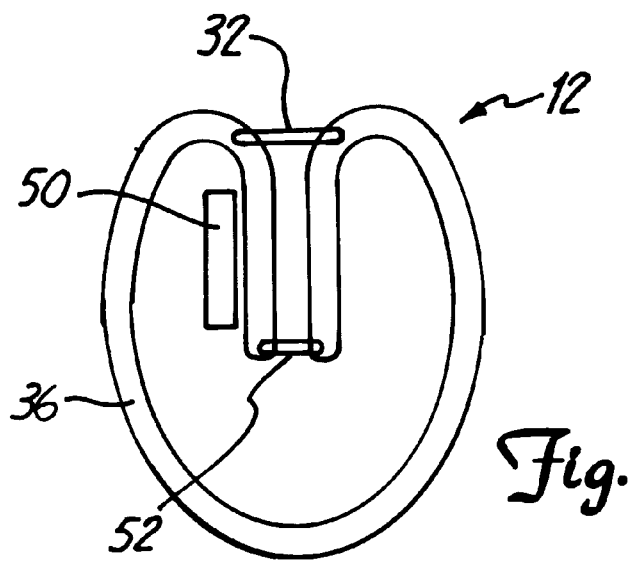
FIG. 3A is a cross-sectional view taken along the line labeled 3A—3A in FIG. 1 of a main body portion of the annuloplasty ring.
Figure 3B:
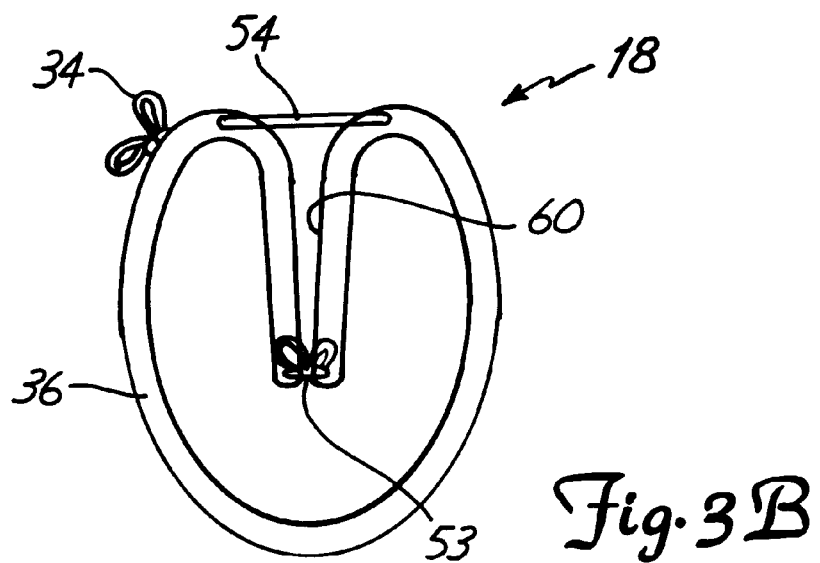
FIG. 3B is a cross-sectional view taken along the line labeled 3B—3B of FIG. 1 of a secondary body of the annuloplasty ring.

FIG. 3A is a side cross-sectional view of annuloplasty ring 10 taken along the line labeled 3A—3A in FIG. 1. As shown in FIG. 3A, in one embodiment, main body 12 includes a core 50 covered by outer layer 36. Typically, core 50 comprises silicone or other biocompatible material, such as a metal, like stainless steel, or plastic such ultra high molecular weight polyethylene and outer layer 36 comprises a fabric sheath made of polyester, PTFE or other materials such as pericardial tissue. Layer 36 is secured by sutures 52 and 54. FIG. 3B is a cross-sectional view of secondary body 18 taken along the line labeled 3B—3B of FIG. 1. As shown in FIG. 3B, core 50 preferably does not extend into secondary body 18. Core 50 preferably does not extend beyond markers 14 and 16 of main body 12.

During surgery, the surgeon can select to use the full annular configuration of annuloplasty ring shown in FIG. 1 or the partial annular configuration shown in FIG. 2. If the surgeon decides that a partial annular configuration annuloplasty ring is desirable, a scalpel or other sharp instrument or a cauterizing device may be used to cut the annuloplasty ring at the markers 14 and 16, or at any point(s) therebetween. Markers 14 and 16 provide a visible indicator for the surgeon when severing the annuloplasty ring as well as enable proper sizing of the ring within the annulus. In one embodiment, markers 14 and 16 are formed by wrapping a suture around the ring 10. When forming the partial annular ring of FIG. 2, portion 40 may be discarded and the remaining partial annular configuration implanted around the posterior leaflet annulus of the patient's heart.

Figure 4:
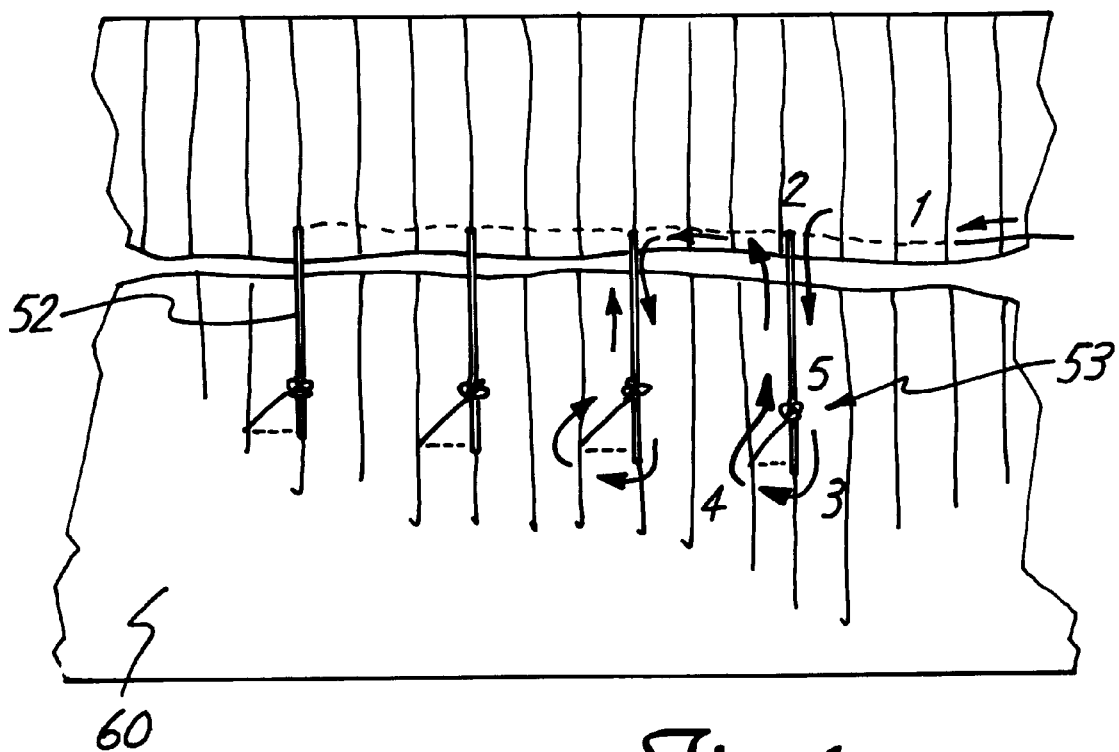
FIG. 4 is a top plan view of a portion of the annuloplasty ring showing a suture used to form a cut zone.
Figure 5:
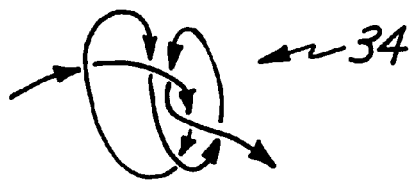
FIG. 5 is a diagram of a suture knot used with the suture of FIG. 4.

FIG. 4 is a top plan view of inner fabric layer 60 showing suture 52 and inside knots 53. Arrows provided in FIG. 4 illustrate the direction of suturing. In one preferred embodiment, knot 53 comprises a double cinch knot as shown in FIG. 5. Between points 1 and 2 shown in FIG. 4, suture 52 extends under layer 60. From point 2 to point 3, suture 52 extends over layer 60 and across the gap formed between the two sides of layer 60. From point 3 to point 4, suture 52 is threaded under layer 60 and over from point 4 to point 5. Knot 53 is formed at point 5 and suture 52 is brought back across the fabric to the opposite side of layer 60 and the process is repeated.

Figure 6A:
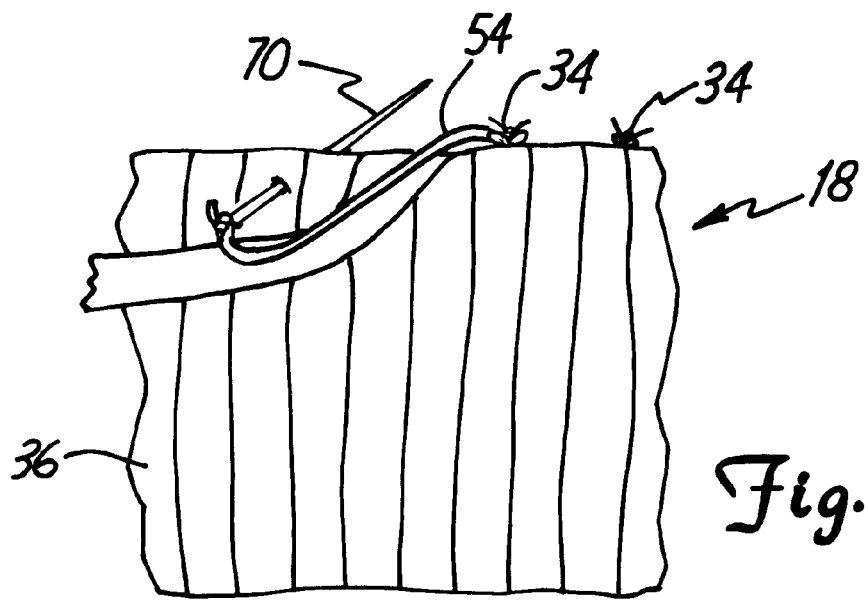
FIGS. 6A and 6B are side plan views showing steps in the manufacture of the annuloplasty ring of FIG. 1.
Figure 6B:
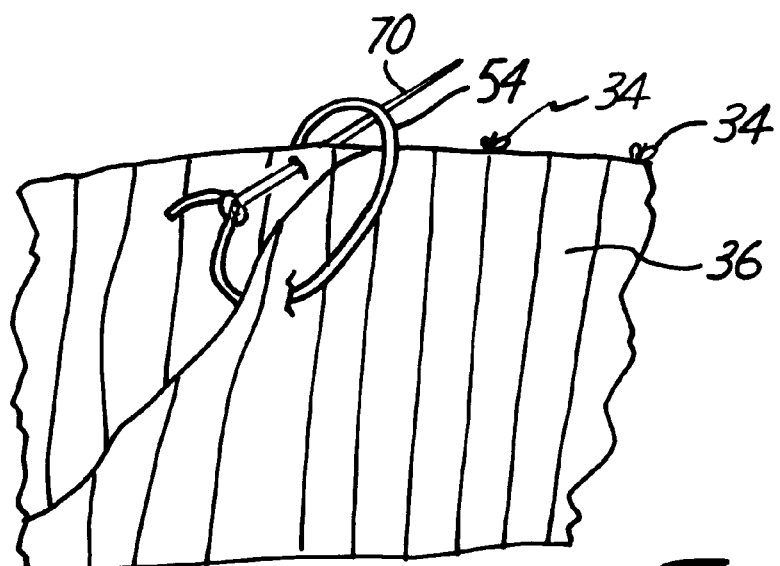

FIGS. 6A and 6B are side plan views showing steps in forming stitches 34. As shown in FIG. 6A, the fabric of body 18 is brought together and suture 54 is threaded through the fabric using needle 70. As shown in FIG. 6B, suture 54 is brought back around through both fabric layers and under itself to form stitch 34. Preferably, this is done in a manner to leave a relatively long portion of suture 54 exposed to thereby mark the cut zone. Further, as every stitch includes a knot, the cut zone will not fray if it is severed.

In addition to markings 14 and 16, elongated stitches 34 are also visible along the length of secondary body 18 and provide an indication of the cut zone region.

Thus, the present invention provides a single annuloplasty ring which may be selectively configured either as a full annuloplasty ring or as a partial annuloplasty ring. Another feature of the present invention is that when the partial configuration is selected by the surgeon, the surgeon has the ability to select the length of the outer circumference. Specifically, a surgeon may determine that only a small portion of the secondary body should be removed leaving a partial annular configuration that provides an outer circumference of any desired length, including an outer circumference which is almost completely closed. Furthermore, in yet another aspect of the present invention, the secondary body may be severed at a single location.

Although the present invention has been described with reference to preferred embodiments, workers skilled in the art will recognize that changes may be made in form and detail without departing from the spirit and scope of the invention. For example, the core can extend into the cut zone and the ring may be a rigid ring and is not limited to the flexible material or fabrics set forth herein.

What is claimed is:

1. An annuloplasty ring, comprising:

an elongated main body portion having a generally partial annuloplasty shape extending between a first end and a second end, the main body made of a biocompatible material;

an elongated secondary body portion having a first end and a second end extending between, respectively, the first and the second ends of the elongated main body portion, the secondary body portion made of a cutable coreless biocompatible fabric material and fabricated to allow cutting therein without fraying of the secondary body; and a first cut zone marker which couples the first end of the main body portion to the first end of the secondary body portion;

a second cut zone marker which couples the second end of the main body portion to the second end of the secondary body portion;

wherein at least a portion of the secondary body portion is selectively removable by severing at any two locations between the first cut zone marker and the second cut zone marker, thereby forming a non-fraying annuloplasty ring having a generally partial annuloplasty ring shape.

2. The annuloplasty ring of claim 1 wherein the secondary body includes a body retaining member to maintain integrity of the first end of the main body portion when the first cut zone is severed.

3. The annuloplasty ring of claim 2 wherein the main body portion includes a fabric layer and the body retaining member substantially prevents fraying of the fabric layer.

4. The annuloplasty ring of claim 2 wherein the body retaining member comprises a suture.

5. The annuloplasty ring of claim 4 wherein the suture is knotted.

6. The annuloplasty ring of claim 5 wherein the knotted suture forms a visual pattern to mark the first cut zone marker and the second cut zone marker.

7. The annuloplasty ring of claim 1 wherein the elongated main body portion includes a core.

8. The annuloplasty ring of claim 7 wherein the core does not extend between the first cut zone marker and the second cut zone marker.

9. The annuloplasty ring of claim 1 wherein the main body comprises a substantially flexible material.

10. An annuloplasty prosthesis, comprising:

an annuloplasty ring including a main body and a secondary body, the secondary body formed of a cutable coreless biocompatible fabric material, wherein a portion of the annuloplasty ring may be selectively severed in a cut zone region to form a non-fraying partial annuloplasty ring shape;

first and second markers which provide a visual indication of the location of the cut zone; and a suture extending through the material in the cut zone region and having a plurality of knots to prevent fraying if the cut zone region is severed.

11. The annuloplasty prosthesis of claim 10 wherein the plurality of knots include elongated stitches which are visible to thereby mark the cut zone region.

12. The annuloplasty prosthesis of claim 10 including an annular core extending at least partially through the annuloplasty ring.

13. The annuloplasty prosthesis of claim 10 wherein the material comprises fabric.

14. The annuloplasty prosthesis of claim 10 wherein the biocompatible material comprises a substantially flexible material.

* * * * *